United States Patent

Adachi et al.

[11] Patent Number: 6,034,100
[45] Date of Patent: *Mar. 7, 2000

[54] METHOD FOR INHIBITING CYTOKINE SECRETION

[75] Inventors: Masakazu Adachi, Takasaki; Hisashi Tamaoka, Tokushima; Yukihisa Ono, Tokushima; Kazunori Omori, Tokushima, all of Japan

[73] Assignee: Otsuka Pharmaceutical Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/523,810

[22] Filed: Sep. 5, 1995

Related U.S. Application Data

[63] Continuation-in-part of application No. PCT/JP94/00266, Feb. 22, 1994.

[30] Foreign Application Priority Data

Mar. 10, 1993 [JP] Japan ..................... 5-048501
Sep. 2, 1994 [JP] Japan ..................... 6-209518

[51] Int. Cl.[7] .......................... A61K 31/47; A61K 31/495
[52] U.S. Cl. ........................... 514/312; 514/314; 514/255
[58] Field of Search ...................... 514/312, 314, 514/255

[56] References Cited

U.S. PATENT DOCUMENTS 4,399,134  8/1983  Ishikawa et al. ......................... 424/246
4,894,374  1/1990  Skotnicki et al. ..................... 514/230.5

FOREIGN PATENT DOCUMENTS 0 287 651  10/1988  European Pat. Off. .
     36177   4/1990  European Pat. Off. .
   2407744   3/1974  Germany .
   3420116  12/1985  Germany .
   3632222   4/1988  Germany .
   3641312   6/1988  Germany .
 63-152318   6/1988  Japan .
   2095668  10/1982  United Kingdom .
 WO 91/07401  5/1991  WIPO .

OTHER PUBLICATIONS

J. Antimicrob. Chemother., 19 (No. 6), pp. 781–790 (1987).
Int. J. Immunopharmacol, 12 (No. 1), pp. 31–36 (1990).
Drug Safety, 6 (No. 1), pp. 8–27 (1991).
J. Chemother., (Florence) 1990, 2)5), pp. 300–305.
J. Antimicrob. Chemother., 1992, 30 (2), pp. 240–242.
J. Infect. Dis., 1985, 152 (4), pp. 811–816.
Antimicrob. Agents Chemother. 1986, 30 (1), pp. 184–186.

*Primary Examiner*—Theodore J. Criares
*Attorney, Agent, or Firm*—Sughrue, Mion, Zinn, Macpeak & Seas, PLLC

[57] ABSTRACT

A method for the prophylaxis and treatment of diseases induced by acceleration of secretion of cytokines (e.g. TNF-α, IL-1, IL-6, IL-8, and IFN-γ) which comprises administering a benzoheterocyclic compound of the formula:

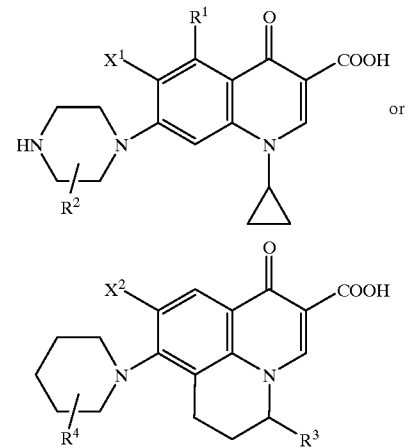

wherein $R^1$ and $R^2$ are lower alkyl and $X^1$ is halogen, $R^3$ is lower alkyl, $R^4$ is hydroxy, and $X^2$ is halogen, or a pharmaceutically acceptable salt thereof.

3 Claims, No Drawings

METHOD FOR INHIBITING CYTOKINE SECRETION

CROSS-REFERENCE TO RELATED APPLICATIONS

This application is a continuation-in-part of International Application No. PCT/JP94/00266 designating also the U.S.A. (filed on Feb. 22, 1994, and now pending), herein incorporated by reference.

FIELD OF THE INVENTION

This invention relates to a cytokine inhibitor, more particularly an agent for inhibiting various cytokines such as tumor necrosis factor-α (TNF-α), interleukin-1 (IL-1), interleukin-6 (IL-6), interleukin-8 (IL-8), interferon-γ (IFN-γ), which comprises as an active ingredient at least one of benzoheterocyclic compounds selected from 1,4-dihydro-4-oxoquinoline-3-carboxylic acids or a salt thereof and 6,7-dihydro-1-oxo-1H,5H-benzo[i,j]quinolidine-2-carboxylic acids or a salt thereof.

BACKGROUND OF THE INVENTION

There have been found various proteins, called cytokines, which inhibit biological response such as immunoresponse, inflammatory reaction and hemopoietic function. As the structures and activities of cytokines have gradually been clarified, it has also been made clear that they posses a wide spectrum of immunological and nonimmunological activities and have much relevance to cell growth, differentiation, homeostasis and pathological physiology.

Among the cytokines, TNF-α has been found as an anti-tumor cytokine and has been expected to be useful as an antitumor agent. However, later on it was found that it is identical with cachectin which is a cachexy-inducing factor. It is reported that TNF-α has an activity of stimulating production of other cytokines such as IL-1, etc., proliferative activity of fibroblast, endotoxin shock-inducing activity, an activity of promoting the adhesion of leukocytes to endothelium by increasing intercellular adhesion molecules (ICAM-1, ICAM-2) or endothelial leukocyte adhesion molecule-1 (ELAM-1) [cf. Beutler, B., et al., Nature, 316, 552–554 (1985); Peetre, C., et al., J. Clin. Invest., 78, 1694–1700 (1986); Kurt-Jones, E. A., et al., J. Immunol., 139, 2317–2324 (1987); Bevilacqua, M. P., et al., Science, 241, 1160–1165 (1989); Akatu, K. & Suda, T., Medical Practice, 8 (9), 1393–1396 (1991)].

Moreover, it is reported that in bacterial or parasitic infectious diseases, TNF-α is contained in a higher concentration in blood and cerebrospinal fluid [cf. Mituyama, M., IGAKU-NO-AYUMI, 159 (8), 467–470 (1991); and Nakao, M., IGAKU-NO-AYUMI, 159 (8), 471–474 (1991)]. It is also reported that in rheumatoid arthritis, the joint fluid and blood serum have TNF-A activity [cf. Saxne, T., et al., Arthritis Rheum., 31, 1041 (1988); Chu, C. Q., et al., Arthritis Rheum., 34, 1125–1132 (1991); Macnaul, K. L., et al., J. Immunol., 145, 4154–4166 (1990); Brennan, F. M., et al., J. Immunol., 22, 1907–1912 (1992); and Brennan, F. M., et al., Bri. J. Rheum., 31, 293–298 (1992)].

It is further reported that in patients suffered from a severe respiratory diseases: adult respiratory distress syndrome (ARDS), the phlegm of the patients contain an increased TNF-α [cf. Millar, A. B., et al., Nature, 324, 73 (1986)], and that TNF-α participates also in the severity of virus hepatitis [cf. Muto, Y. et al., Lancet, ii, 72–74 (1986)].

It is also reported that the blood concentration of TNF-α raises in case of myocardial ischemia (e.g. acute myocardial infarction) [cf. Latini, R., et al., J. Cardiovasc. Pharmacol., 23, 1–6 (1994)], and it is suggested that TNF-α will participate in such diseases [cf. Lefer, A. M., et al, Science, 249, 61–64 (1990). It is recently reported that TNF-α inhibits myocardial contraction (cf. Finkel, M. S., et al., Science, 257, 387–389 (1992); and Pagani, D. F., et al., J. Clin. Invest., 90, 389–398 (1992)].

As to Interleukin-1 (IL-1), it has been decided in the 2nd International Limphokine Workshop that the uniform designation "interleukin-1" is given to the physiologically active substance which had been called by various names such as Lymphocyte Activating Factor (LAF), Mitogenic Protein, Helper peak-1, T-cell replacing factor III (TRF-III), T-cell replacing factor macrophage (TRFM), B-cell activating factor, B-cell differentiation factor. [cf. Cellular Immunol., 48, 433–436 (1979)]. This is decided by the reason that the above physiologically active substance having various namings could not be distinguished from each other and had been designated merely based on different angles of the physiological activities.

It has been known that the above IL-1 is a biomaterial which is important for inducing and transmitting the systemic biological response against infection and inflammation, and further this substance per se has a strong antitumor activity [cf. Hirai, Y., et al.; "Gann Monograph on Cancer Research", Japan Scientific Societies Press, Tokyo (1988)], and further it has also been found that it induces response observed in the inflammation in vivo, such as fever, increase of leukocytes, activation of lymphocytes, induction of biosynthesis of acute phase protein in liver [cf. Dinarello, C. A.; Interleukin-1, Rev. Infect. Des., 6, 51–95 (1984), and Kluger, M. J., Oppenheim, J. J. & Powanda, M. C.; The Physiologic, Metabolic and Immunologic Actions of Interleukin-1, Alan R. Liss, Inc., New York (1985)].

Moreover, IL-1 has various biological activities and has been considered to be an important factor for maintaining the homeostasis, but when the function of IL-1 production is disordered and thereby IL-1 is produced in an abnormally larger amount, it may cause various diseases. For example, it has been reported that in case of rheumatoid arthritis, there is a strong correlation between the degree of inflammation of articular synovium and the degree of the bone destruction and expression of HLA-DR antigen in the synovial tissue [cf. Miyasaka, N., Sato, K., Goto, M., Sasano, M., Natsuyama, M., Inoue, K., and Nishioka, K.; Augmented Interleukin-1 Production and HLA-DR Expression in the Synovium of Rheumatoid Arthritis Patient: Arthritis Rheum., 32, (4), 476–480 (1988)].

Accordingly, it is considered that the various physiological properties associated with IL-1 may be blocked by inhibiting the excess release of IL-1 from cells. There are used glucocorticoid hormones for the treatment of chronic inflammatory diseases, and it is known that the activities will partly be due to the suppression of IL-1 production [cf. Lew, W., Oppenheim, J. J., & Matsushima, K.; Analysis of the Suppression of IL-1α and IL-1β Production in Human Peripheral Blood Mononuclear Adherent Cells by a Glucocorticoid Hormone: J. Immunol., 140, (6), 1895–1902 (1988)]. However, it has been known that glucocorticoids induce disadvantageously various heavy side effects owing to its various physiological activities.

In the course of proliferation of B cells activated by antigen stimulation and the differentiation thereof into antibody-producing cells, some cytokines will act. As the cytokines participating in the proliferation there are known interleukin-4 and -5 which correspond to B cell growth factor-I and -II (BCGF-I and BCGF-II), respectively, and as the cytokines participating in the differentiation, there is known interleukin-6 (IL-6) which is B cell differentiation factor (BCDF).

The above IL-6 has firstly been found as a factor for inducing the production of immunoglobulin in B cell line transformed with EB virus in a supernatant of culture broth of peripheral blood monocytes, and thereafter it has been studied independently as various factors such as B cell stimulatory factor-2 (BSF-2), interferone-β2 (IFN-β2), 26 kDa protein, hepatocytes stimulatory factor, hybridoma plasmacytoma growth factor (HPGF), but it was found by Hirano et al. in 1986 that all of these cytokines are identical by cloning of them [cf. Hirano, T., et al, Nature, 324, 73 (1986)].

It has been clarified that IL-6 plays an important role in an antibody production in B cell but also is an important factor in hemopoietic system, nervous system and protective system of biobody (e.g. liver) as well as in immune system, for example, it is effective for inducing proliferation and differentiation of T cell, inducing production of protein at acute phase by acting on hepatic cells, promoting formation of pluripotential colony to the hemopoietic cells, and the like.

There are various reports concerning IL-6, its production and correlation between abnormal secretion thereof and various diseases as follows.

In various autoimmune diseases such as hypergammaglobulinemia, chronic articular rheumatism being positive in various autoantibodies, systemic lupus erythematosus, etc., polyclonal activation of B cells is induced and thereby a large amount of IL-6 is present in the joint fluid of the patients suffered from rheumatoid arthritis and IL-6 is produced by the activated T cells and B cells which are penetrated into synovium tissue [cf. Hirano, et al., Eur. J. Immunol., 18, 1797 (1988)].

It is also reported that in patients suffered from atrial myxedema having autoimmune disease-like symptom, the clinical symptom disappears by removing the tumor, from which it is assumed that the symptom will be induced by any factor produced by tumor cells. It is also suggested that IL-6 will be largely produced by these tumor cells and there is a certain correlation between the abnormal production of IL-6 and the abnormal state of polyclonal B cells [cf. Hirano, T., et al., Proc. Natl. Acad. Sci., USA, 82, 5490 (1985)].

It has already been reported that IL-6 is a factor of increasing plasmacytoma in mouse, and the increase of plasmacytoma in myeloma cells isolated from the human patient suffered from multiple myeloma could be inhibited by anti-IL-6 antibody, and therefore, it is made clear that IL-6 may probably be an autogrowth factor of myeloma cells, and thereby it is suggested that IL-6 participates largely not only in the development of the abnormal state of polyclonal B cells but also in the development of the abnormal state of monoclonal B cells such as myeloma cells [cf. Kawano, M., et al., Nature, 332, 83 (1988)].

In Castleman's disease accompanied with tumor of lymph node of which cause is unknown, high blood level of IL-6 activity is observed, and further, hypergammaglobulinemia or high level of protein in acute phase are also observed. The blood level of IL-6 becomes normal by removing the tumor of lymph node and thereby the clinical symptom is also recovered [cf. Yoshizaki, K., et al., Blood, 74, 1360 (1989)].

High IL-6 activity is observed in urine of patients suffered from primary glomerular nephritis, which activity is significantly higher than that in healty persons or in patients suffered from a minimal change nephrotic syndrome. The IL-6 activity in urine is correlative to the degree of growth of mesangial cells in tissue specimen of renal biopsy. In fact, when IL-6 is added to the culture system of rat renal mesangial cells in vitro, growth of cells is induced dependently on the concentration of IL-6, and thereby, it was made clear that IL-6 is a growth factor of mesangial cells [cf. Horii, Y., et al., J. Immunol., 143, 3949 (1989)].

Interleukin-8 (IL-8) is also called as a neutrophil activator and is a basic heparin-binding polypeptide having 72 amino acids. It is a cytokine produced by various tisse cells (not only by activated macrophage).

IL-8 is (1) a chemotactic factor to neutrophil, T cell and basophil, and has various physiological activities such as (2) activation of neutrophil and acceleration of release of lysozyme, change of adhesion of neutrophil to endothelium of blood vessel, and inhibition of growth of Candida, (3) break of the joint synovilis accompanying damping of neutrophil by injection of IL-8 into joint, (4) increase of generation of adhesion factor on neutrophil, (5) control of the histamine release in basophil, and (6) activation of neutrophil in an artificial organs. Besides, IL-8 is also called as—inflammatory cytokine, and it is considered that inflammatory diseases will be caused by abnormal production of IL-8 and excess response to IL-8.

Interferon-γ (IFN-γ) has firstly been reported by Wheelock in 1965 and is produced by stimulating immunocompetent cells such as T cells or natural killer cells, etc. by a specific or non-specific antigen and is rather recognized as a sort of immunomodulator than an antiviral activator [Arai, S., Akaji, A., RINSHO-MENEKI, 25 (5), 547–553 (1993)]. INF-γ participates in Shwartzman reaction. (This reaction is an inflammatory reaction accompanied with bleeding and necrosis at the injected portion when a filtrated fluid of a culture of bacteria is subcutaneously injected and the same fluid is intravenously injected after about 20 hours, and when both injections of said fluid are done by intravenous route, various organs such as kidney, liver, lung, heart, etc. are damaged. This phenomenon has been found by G. Sanarelli, and hence, it is also called as "Shwartzman-Sanarelli phenomenon"). It is reported that anti-INF-γ antibody inhibits said Shwartzman reaction [cf. Alfons Billian, Immunology Today, 9, 37–40 (1988)]. It is reported that in patients suffered from systemic lupus erythematosus, the concentration of INF-γ in blood serum is increased, and that the concentration of INF-γ is increased also in the blood serum of patients suffered from Sjogren's syndrome and polymyalgia rheumatica [cf. M. AL-Janadi, S. AL-Balla, A. AL-Dalaan, and S. Raziuddin, J. Clin. Immunol., 13, 58–67 (1993)], and further that when INF-γ is injected to patients suffered from multiple sclerosis, the symptom becomes worse [cf. H. S. Panitch and C. T. Bever, Jr., J. Neuroimmunol., 46, 155–164 (1993)].

In order to treat the various diseases which may be caused by the cytokines as mentioned above, it has been considered to use a cytokine inhibitor.

By the way, the 1,4-dihydro-4-oxoquinoline-3-carboxylic acids of the formula (I) as shown hereinafter and the 6,7-dihydro-1-oxo-1H,5H-benzo[i,j]quinolidine-2-carboxylic acids of the formula (II) as shown hereinafter are disclosed in European Patent Publication 0287951 and U.S. Pat. No. 4,399,134 as antibacterial agents.

It is disclosed in DE-3,632,222-A that 4-oxo-quinoline-carboxylate derivatives including some compounds of the present invention are useful to treat a wide variety of diseases and infections in humans (e.g. bone and joint infections, post-operative wound infections, infections after dental operations, septic arthritis, mastitis, tonsilitis and genital and eye infections) and animals, but it does not mentioned as to the cytokine inhibiting activities.

It is disclosed in DE-3,641,312-A that 7-amino-4-oxo-quinoline-carboxylate derivatives including some compounds of the present invention are useful as antibacterials and immunostimulants, but it does not mention as to the cytokine inhibiting activities.

It is disclosed in EP-361,177-A that 6-halo-4-quinolone compounds analogous to the compounds of the present invention are useful in the treatment of rheumatoid arthritis, but it does not mention as to the cytokine inhibiting activities.

It is disclosed in DT-2,407,744 that (5-tetrazolyl)-4-quinolone-3-carboxamides analogous to the compounds of the present invention are useful for treating extrinsic asthma, hay fever, urticaria, eczema and atopic dermatitis, but it does not mention as to the cytokine inhibiting activities.

It is disclosed in GB-2,095,668 that acyl substituted quinolone-carboxylic acid derivatives analogous to the compounds of the present invention are useful as antiallergic agents, but it does not mention as to the cytokine inhibiting activities.

It is disclosed in JP-63–152,318-A that pyridone-carboxylic acid compounds analogous to the compounds of the present invention are useful as antimycoplasma agents effective against mycoplasma infectious diseases such as human penumonia or arthritis, cattle mastitis, chicken chronic diseases of the respiratory system, but it does not mention as to the cytokine inhibiting activities.

It is disclosed in DE-3,420,116-A that 1-cyclopropyl-1,4-dihydro-4-oxo-quinoline-3-carboxylic acids analogous to the compounds of the present invention are useful for the treatment of immunlogical impairment due to infection, age, tumours or treatment with cytostatics, but it does not mention as to the cytokine inhibiting activities.

Furthermore, the following literatures disclose that some compounds analogous to the compounds of the present invention show IL-1 production inhibitory activity, and immune inhibitory activities:

Roche Y.; Gougerot Pocidalo M. A.; Fay M.; Etienne D.; Forest N.; and Pocidalo J. J.; J. Antimicrob. Chemother., 19 (No.6), pp. 781–790 (1987)

Bailly S.; Fay M.; Roche Y.; and Gougerot Pocidalo M. A.; Int. J. Immunopharmacol., 12 (No. 1), pp. 31–36 (1990)

Paton J. H.; and Reeves D. S.; Drug Safety, 6 (No. 1), pp. 8–27 (1991)

Tawfik A. F.; Shoeb H. A.; Bishop S. J.; Al-Shammary F. J.; and Shibl A. M.; J. Chemother., (Florence) 1990, 2 (5), pp. 300–305

Anjo Saeko; Kondo Yuriko; Ishiboshi Yoshio; and Arai Toshihiko; J. Antimicrob. Chemother., 1992, 30 (2), pp. 240–242

It is also disclosed in the following literatures that some analogous compounds have anti-arthritis activity: Bayer, Arnold S.; Norman, Dean C.; and Anderson, Debbie; J. Infect. Dis., 1985, 152 (4), pp. 811–816, and Bayer, Arnold S.; Norman, Dean C.; Blomquist, Ingrid K.; Antimicrob. Agents Chemother. 1986, 30 (1), pp. 184–6.

DISCLOSURE OF THE INVENTION

The present inventors have studied to develope a new cytokine inhibitor and have found that the benzoheterocylic compounds of the formulae (I) and (II) as shown below, particularly 7-(3-methyl-1-piperazinyl)-1-cyclopropyl-6-fluoro-5-methyl-1,4-dihydro-4-oxoquinoline-3-carboxylic acid or a salt thereof and 9-fluoro-8-(4-hydroxy-1-piperidinyl) -5-methyl-6,7-dihydro-1-oxo-1H,5H-benzo[i,j] quinolidine-2-carboxylic acid or a salt thereof are useful as a cytokine inhibitor, particularly a TNF-α inhibitor, an IL-1 inhibitor, an IL-6 inhibitor, an IL-8 inhibitor, and an interferon-γ inhibitor.

1,4-Dihydro-4-oxoquinoline-3-carboxylic acids (I):

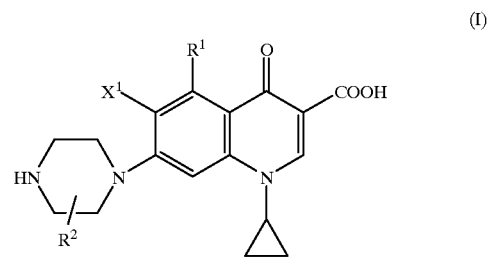

(I)

wherein $R^1$ and $R^2$ are each a lower alkyl group and $X^1$ is a halogen atom.

6,7-Dihydro-1-oxo-1H,5H-benzo[i,j]quinolidine-2-carboxylic acids (II):

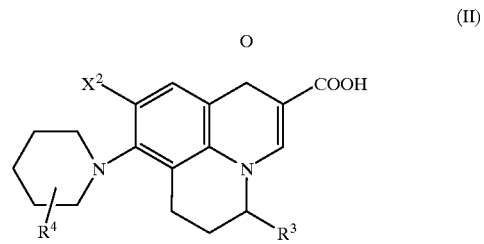

(II)

wherein $R^3$ is a lower alkyl group, $R^4$ is hydroxy group, and $X^2$ is a halogen atom, or a salt thereof.

An object of the invention is to provide a novel cytokine inhibiting agent. Another object of the invention is to provide a new use of the known benzoheterocyclic compounds of the formulae (I) and (II) and their salts as a cytokine inhibitor, particularly as TNF-α inhibitor, IL-1 inhibitor, IL-6 inhibitor, IL-8 inhibitor, and IFN-γ inhibitor. A further object is to provide a method for the prophylaxis and treatment of various diseases induced by acceleration of cytokine secretion by administering an effective amount of the benzoheterocyclic compounds (I) or (II) or a salt thereof to the subject suffering from such diseases.

When the cytokine inhibitor is used as a TNF-α inhibitor, it is used for the prophylaxis and treatment of various diseases accompanied by the abnormal production or excretion of TNF-α, particularly rheumatoid arthritis, endotoxin shock, adult respiratory distress syndrome, myocardial infarction which is syndrome of myocardial ischemia. It is also used in the coronary artery bypass grafting.

The IL-1 inhibitor is useful for the prophylaxis and treatment of various diseases induced by acceleration of interleukin-1 secretion, for example, autoimmune diseases such as nephritis, vasculitis, and inflammatory bowel disease (e.g. ulcerative colitis or Crohn's disease); rheumatic diseases such as rheumatoid arthritis, psoriatic arthritis, scleroderma, Behget's disease, and gout; inflammatory diseases associated with local and systemic infection such as septic shock and inflammatory diseases in dental, ophthalmic and otorhinolic fields such as chronic periodontal disease, ocular inflammatory disease, and otitis media; allergic diseases such as asthma; osteoporosis; endometriosis [cf.

Fukih, H. et al; Fertil. Sterl., 47, p213 (1987)]; chronic granulomatous disease; Hodgkin's disease; acute or chronic myelogenous leukemia; graft-vs.-host disease; diabetes [cf. Dayer Metroz M. -D.; Eur. J. Clin. Invest., 22 (No. 4), p2, A50 (1992)]; Kawasaki's disease [cf. Leung, D. Y. M. et al; J. Exp. Med., 164, p1958 (1986)]; and the like.

The IL-6 inhibitor is useful for the treatment of various diseases induced by secretion and production of IL-6, for example, cancerous cachexie, atrial myxedema, rheumatoid arthritis, autoimmune diseases, Castleman's disease, myeloma, Lennert lymphoma, mesangial proliferative nephritis, psoriasis, Kaposi's sarcoma accompanied with AIDS, postmenopausale osteoporosis, and the like.

The IL-8 inhibitor is useful for the prophylaxis and treatment of acute or chronic inflammatory diseases by the activity of inhibiting the production of IL-8. It is also useful for enhancing the bio-adoptability of artificial organs and artificial blood vessel. The inflammatory diseases to be treated by the IL-8 inhibitor of this invention include inflammatory skin diseases such as inflammatory keratosis (e.g. psoriasis, etc.), atopic dermatitis, contact dermatitis, and the like; autoimmune diseases such as rheumatoid arthritis, systemic lupus erythematosus (SLE), Behcet's disease, which are chronic inflammatory diseases; inflammatory intestine diseases such as Crohn's disease, ulcerative colitis, and the like; inflammatory hapatic diseases such as hepatitis B, hepatitis C, alcoholic hepatitis, chemicl allergic hepatitis, and the like; inflamatory kidney diseases such as glomerulonephritis, and the like; inflammatory respiratory diseases such as bronchitis, and the like; aphtha; vocal fold inflammation; inflammatory diseases occurred during using artificial organs or artificial blood vessel; and the like, but are not limited thereto.

Moreover, the IL-8 inhibitor of the invention has also an inhibitory activity of the promotion of production of IL-8 by *Helicobacter pylori* (hereinafter, referred to as "*H. pylori*") from IL-8 producing cells (e.g. peripheral blood monocyte, tissue macrophase, large granular lymphocyte, T-lymphocyte, neutrophile, fibroblast, vascular endogenic cells, cutaneous keratinocyte, hapatic cells, astrocyte, epithelial cells, gastric carcinoma cells, etc.) and hence is useful for the prevention of occurrence or recurrence of gastric mucous membrane disorder which are induced by *H. pylori.*

The IFN-γ inhibitor is useful for the treatment of various diseases induced by the production of IFN-γ, for example, endotoxin shock; inflammation accompanied with topical or systemic infectious diseases such as septicemia; rheumatoid arthritis; collagen diseases such as systemic lupus erythematosus (SLE); central nervous chronic inflammatory diseases such as multiple sclerosis; and the like.

The each group in the formulae (I) and (II) denotes as follows.

The "lower alkyl group" denotes a straight chain or branched chain alkyl group having 1 to 6 carbon atoms, such as methyl, ethyl, propyl, isopropyl, butyl, tert-butyl, pentyl, hexyl, and the like.

The "halogen atom" denotes fluorine, chlorine, bromine or iodine atom.

Among the benzoheterocyclic compounds of the formulae (I) and (II), basic compounds can easily form a salt with conventional pharmaceutically acceptable acids. These acids include, for example, inorganic acids such as sulfuric acid, nitric acid, hydrochloric acid, phosphoric acid, hydrobromic acid, etc., and organic acids such as acetic acid, p-toluenesulfonic acid, ethanesulfonic acid, oxalic acid, maleic acid, fumaric acid, malic acid, tartaric acid, citric acid, succinic acid, benzolic acid, etc. Besides, among the benzoheterocyclic compounds of the formulae (I) and (II), acidic compounds can easily form a salt with conventional pharmaceutically acceptable basic compounds. These basic compounds include, for example, metal hydroxides such as sodium hydroxide, potassium hydroxide, lithium hydroxide, calcium hydroxide, etc., alkali metal carbonates or hydrogen carbonates such as sodium carbonate, potassium hydrogen carbonate, sodium hydrogen carbonate, etc., and alkali metal alcoholate such as sodium methylate, potassium ethylate, etc.

The compounds of the formulae (I) and (II) and their salts of this invention are used in the form of a conventional pharmaceutical preparation in human being and other animals. The preparation is prepared by using conventional diluents or carriers such as fillers, thickening agents, binders, wetting gents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (solutions, emulsion, suspensions, etc.), and the like. In order to form in tablets, there are used conventional carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets.

In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like.

Capsules can be prepared by charging a mixture of the compound of this invention with the above carriers into hard gelatin capsules or soft capsules in a usual manner.

In the preparation of injections, the solutions, emulsions or suspensions are sterilized and are preferably made isotonic with the blood. In the preparation of these solutions, emulsions and suspensions, there are used conventional diluents, such as water, macrogol, ethyl alcohol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose or glycerin in an amount sufficient to make them isotonic, and may also be incorporated with conventional solubilizers, buffers, anesthetizing agents.

Besides, the pharmaceutical preparations may optionally be incorporated with coloring agents, preservatives, perfumes, flavors, sweetening agents, and other medicaments, if desired.

The amount of the active compound to be incorporated into the cytokine inhibiting agent of this invention is not specified but may be selected from a broad range, but it is usually in the range of 1 to 70% by weight, preferably about 1 to 30% by weight.

The cytokine inhibiting preparation of this invention may be administered in any method, and suitable method for administration may be determined in accordance with various forms of preparation, ages, sexes and other conditions of the patients, the degree of severity of diseases, and the like. For example, tablets, pills, solutions, suspensions, emulsion, granules and capsules are administered orally. The injections are intraveneously administered alone or together with a conventional auxiliary liquid (e.g. glucose, amino acid solutions), and further are optionally administered alone in intramuscular, intracutaneous, subcutaneous, or intraperitoneal route, if desired. Suppositories are administered in intrarectal route.

The dosage of the cytokine inhibiting agent of this invention may be selected in accordance with the usage, ages, sexes and other conditions of the patients, the degree of severity of the diseases, and the like, but is usually in the range of about 0.1 to 1000 mg of the active compound of this invention per 1 kg of body weight of the patient per day. The daily dosage may be administered dividedly in one to four times in a day. The active compound is preferably contained in an amount of about 1 to about 600 mg per the dosage unit.

BEST MODE FOR CARRYING OUT THE INVENTION

The present invention is illustrated by the following preparations and pharmacological experiments.

Preparation 1

Film coated tablets are prepared from the following components.

| Components | Amount |
| --- | --- |
| 7-(3-Methyl-1-piperazinyl)-1-cyclopropyl-6-fluoro-5-methyl-1,4-hydroxy-4-oxoquinoline-3-carboxylic acid | 150 g |
| Abicel (tradename of microcrystalline cellulose, manufactured by Asahi Chemical Industry Co., Ltd., Japan) | 40 g |
| Corn starch | 30 g |
| Magnesium stearate | 2 g |
| Hydroxypropyl methylcellulose | 10 g |
| Polyethylene glycol-6000 | 3 g |
| Castor oil | 40 g |
| Ethanol | 40 g |

The active component of this invention, Avicel, corn starch and magnesium stearate are mixed and kneaded and the mixture is tabletted using a conventional pounder (R 10 mm) for sugar coating. The tablets thus obtained are coated with a film coating agent consisting of hydroxypropyl methylcellulose, polyethylene glycol-6000, castor oil and ethanol to give film coated tablets.

Preparation 2

Tablets are prepared from the following components.

| Components | Amount |
| --- | --- |
| 9-Fluoro-8-(4-hydroxy-1-piperidinyl)-5-methyl-6,7-dihydro-1-oxo-1H,5H-benzo[ji]quinolidine-2-carboxylic acid | 150 g |
| Citric acid | 1.0 g |
| Lactose | 33.5 g |
| Dicalcium phosphate | 70.0 g |
| Pluronic F-68 | 30.0 g |
| Sodium laurylsulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium laurylsulfate | 3.0 g |
| Dry magnesium stearate | 3.0 g |
| Ethanol | q.s. |

The active compound of this invention, citric acid, lactose, dicalcium phosphate, Pluronic F-68 and sodium laurylsulfate are mixed. The mixture is screened with No. 60 screen and is granulated in wet with an alcohol solution containing polyvinylpyrrolidone, carbowax 1500 and 6000. If required, an alcohol is added thereto so that the powder mixture is made a paste-like mass. Corn starch is added to the mixture and the mixture is continuously mixed to form uniform particles. The resulting particles are passed through No. 10 screen and entered into a tray and then dried in an oven at 100° C. for 12 to 14 hours. The dried particles are screened with No. 16 screen and thereto are added dry sodium laurylsulfate and dry magnesium stearate, and the mixtue is tabletted to form the desired shape.

The core tablets thus prepared are vanished and dusted with talc in order to guard from wetting. Undercoating is applied to the core tablets. In order to administer the tablets orally, the core tablets are vanished several times. In order to give round shape and smooth surface to the tablets, further undercoating and coating with lubricant are applied thereto. The tablets are further coated with a coloring coating material until the desired colored tablets are obtained. After drying, the coated tablets are polished to obtain the desired tablets having uniform gloss.

Pharmacological experiment

Experiment 1

Method:

A 10% heparinized peripheral blood from healthy volunteer, a test compound and lipopolysaccharide (LPS, 3.3 μg/ml) were suspended in RPMI-1640 medium supplemented with penicillin 100 units/ml and streptomycin 0.1 μg/ml, and the mixture was incubated in a 5% $CO_2$ atmosphere at 37° C. for 18–24 hours. The supernatant of the culture was collected by centrifugation.

The IL-1α and IL-1β isolated from cells by stimulation with LPS were measured by an enzyme-linked immunoassay (ELISA). That is, 96-well ELISA plate was coated with a mouse monoclonal antibody against human IL-1α or human IL-1β, followed by blocking treatment, and thereto was added a test sample and it was subjected to reaction. After the reaction, the plate was washed, and then rabbit polyclonal antibody against IL-1α or IL-1β was added to the plate and subjected to reaction. After washing the plate, horseradish peroxidase (POD)-conjugated anti-rabbit immunoglobulin was added thereto and subjected to reaction. After removing the unbound POD-conjugated antibody by washing, a substrate solution (containing orthophenylenediamine and hydrogen peroxide) was added and subjected to reaction, and thereafter, the absorbance at 492 nm was measured, and thereby the amounts of IL-1α and IL-1β were measured based on each standard curve. The ratio (%) of inhibition of IL-1 release was calculated by the following equation:

IL-1 release inhibitory ratio (%)=100×(1−T/C) wherein T means the amount of IL-1 in the supernatant obtained from the culture solution containing the test compound, and C means the concentration of IL-1 in the supernatant obtained from the culture solution containing the solvent.

Test compounds:
1. 7-(3-Methyl-1-piperazinyl)-1-cyclopropyl-6-fluoro-5-methyl-1,4-dihydro-4-oxoquinoline-3-carboxylic acid.
2. 9-Fluoro-8-(4-hydroxy-1-piperidinyl)-5-methyl-6,7-dihydro-1-oxo-1H,5H-benzo[ji]quinolidine-2-carboxylic acid.

Results:
The results are shown in Table 1.

TABLE 1

| Test compounds | Dose ($3 \times 10^{-5}$ g/ml) | |
|---|---|---|
|  | IL-1α release inhibitory ratio | IL-1β release inhibitory ratio |
| 1 | 93% | 96% |
| 2 | 82% | 78% |

Experiment 2
Method:
The cytokine released from the cells in the same manner as in the above Experiment 1 was measured by the same ELISA method. The concentration of cytokines were determined based upon each standard curve likewise, and the ratio (%) of inhibition of cytokine release was calculated by the following equation:

Cytokine release inhibitory ratio (%)=100×(1−T'/C') wherein T' means the concentration of a cytokine in the supernatant obtained from the culture solution containing the test compound, and C' means the concentration of a cytokine in the supernatant obtained from the culture solution containing the solvent.

Test compound and results:
7-(3-Methyl-1-piperazinyl)-1-cyclopropyl-6-fluoro-5-methyl-1,4-dihydro-4-oxoquinoline-3-carboxylic acid was used as the test compound in an amount of $3 \times 10^{-5}$ g/ml, and the each cytokine release inhibitory ratios were as shown in the following Table 2.

TABLE 2

| Measured cytokines | release inhibitory ratio |
|---|---|
| TNF-α | 39% |
| IL-6 | 59% |
| IL-8 | 24% |
| IFN-γ | 87% |

INDUSTRIAL APPLICATION

The cytokine inhibiting agents of this invention, i.e. INF-α inhibitor, IL-1 inhibitor, IL-6 inhibitor, IL-8 inhibitor and IFN-γ inhibitor, are useful for the prophylaxis and treatment of various diseases induced by acceleration of cytokine secretion, such as autoimmune diseases, rheumatic diseases, various inflammatory diseases, allergic diseases, and the like in human being and other animals.

What is claimed is:
1. A method for treatment of a disease selected from the group consisting of rheumatoid arthritis, adult respiratory distress syndrome, an autoimmune disease, an inflammatory respiratory disease and septicemia, which method comprises administering to a subject afflicted with said disease, a therapeutically effective amount of a benzoheterocyclic compound of the formula (I), or a pharmaceutically acceptable salt thereof:

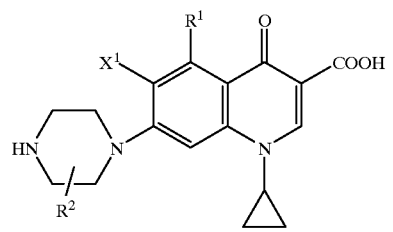

wherein $R^1$ and $R^2$ are each a lower alkyl group and $X^1$ is a haolgen atom.

2. The method according to claim 1, wherein said compound is 7-(3-methyl-1-piperazinyl)-1-cyclopropyl-6-fluoro-5-methyl-1,4-dihydro-4-oxoquinoline-3-carboxylic acid, or a pharmaceutically acceptable salt thereof.

3. The method according to claim 1, wherein said inflammatory respiratory disease is bronchitis.

* * * * *